US008192746B2

(12) United States Patent
Caulfield et al.

(10) Patent No.: US 8,192,746 B2
(45) Date of Patent: Jun. 5, 2012

(54) 15-VALENT PNEUMOCOCCAL POLYSACCHARIDE-PROTEIN CONJUGATE VACCINE COMPOSITION

(75) Inventors: Michael J. Caulfield, Ft. Washington, PA (US); Patrick L. Ahl, Princeton, NJ (US); Jeffrey T. Blue, Telford, PA (US); Jayme L. Cannon, Glenside, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/020,402

(22) Filed: Feb. 3, 2011

(65) Prior Publication Data

US 2011/0195086 A1 Aug. 11, 2011

Related U.S. Application Data

(60) Provisional application No. 61/302,726, filed on Feb. 9, 2010.

(51) Int. Cl.
*A61K 39/385* (2006.01)
(52) U.S. Cl. .................. 424/197.11; 424/193.1
(58) Field of Classification Search .................. None
See application file for complete search history.

(56) References Cited

U.S. PATENT DOCUMENTS

| 5,847,112 A | 12/1998 | Kniskern et al. | |
|---|---|---|---|
| 2003/0180316 A1* | 9/2003 | Boutriau et al. | 424/190.1 |
| 2006/0228380 A1* | 10/2006 | Hausdorff et al. | 424/244.1 |
| 2008/0286838 A1 | 11/2008 | Yuan et al. | |
| 2008/0305127 A1* | 12/2008 | Poolman | 424/194.1 |
| 2009/0035326 A1 | 2/2009 | Contorni et al. | |
| 2009/0317412 A1* | 12/2009 | Alexander et al. | 424/185.1 |

FOREIGN PATENT DOCUMENTS

| CN | 101590224 A | | 12/2009 |
|---|---|---|---|
| WO | 2007000342 | * | 1/2007 |
| WO | 2007071707 | * | 6/2007 |

OTHER PUBLICATIONS

Gonzalez, Be et al,Journal of Pediatric Infectious Disease, vol. 25, pp. 301-305, *Streptococcus pneumoniae* Serogroups 15 and 33.*
Pilishvili, Tamara et al, Journal of Infectious Diseases, Jan. 1, 2010, vol. 201, pp. 32-41, Sustained reductions in invasive pneumococcal disease in the era of conjugate vaccine.*
Park, MK e tal, Clinical and Diagnostic Laboratory Immunology, May 2000, pp. 486-489, vol. 7, No. 3, A latex bead based flow cytometric immunoassay capable of simultaneous type of multiple pneumococcal serotypes (multibead assay).*
Rosenburg, Gerwin D et al, Emerging Infecious Diseases, vol. 16(5), May 2010, pp. 816-823.*

(Continued)

*Primary Examiner* — Albert Navarro
*Assistant Examiner* — Ginny Portner
(74) *Attorney, Agent, or Firm* — Henry P. Wu; Sheldon O. Heber

(57) ABSTRACT

The present invention provides a multivalent immunogenic composition having 15 distinct polysaccharide-protein conjugates. Each conjugate consists of a capsular polysaccharide prepared from a different serotype of *Streptococcus pneumoniae* (1, 3, 4, 5, 6A, 6B, 7F, 9V, 14, 18C, 19A, 19F, 22F, 23F or 33F) conjugated to a carrier protein, preferably $CRM_{197}$. The immunogenic composition, preferably formulated as a vaccine on an aluminum-based adjuvant, provides broad coverage against pneumococcal disease, particularly in infants and young children.

7 Claims, 3 Drawing Sheets

OTHER PUBLICATIONS

Gilbert, Peter et al, Journal of Clinical Epidemiology, vol. 54, pp. 68-85, 2001, Sieve analysis: methods for assessing from vaccine trial data how vaccine efficacy varies with genotypci and phonotypic pathogen variation.*

Centers for Disease Control and Prevention. "Prevention of Pneumococcal Disease: recommendations of the Advisory Committee on Immunization Practices (ACIP)", MMWR, 1997, vol. 46, No. RR-8, pp. 1-25.

Centers for Disease Control and Prevention. "Direct and Indirect Effects of Routine Vaccination of Children with 7-Valent Pneumococcal Conjugate Vaccine on Incidence of Invasive Pneumococcal Disease", MMWR, 2005, vol. 54, No. 36, pp. 893-897.

Arditii et al., "Three-Year Multicenter Surveillance of Pneumococcal Meningitis in Children: Clinical Characteristics, and Outcome Related to Penicillin Susceptibility and Dexamethasone Use", Pediatrics, 1998, vol. 102, No. 5, pp. 1087-1097.

Dagan et al., "Glycoconjugate Vaccines and Immune Interference: A Review", Vaccine, 2010, vol. 28, pp. 5513-5523.

Hicks et al., Incidence of Pneumococcal disease Due to Non-Pneumococcal Conjugate Vaccine (PCV7) Serotypes in the United States during the Era of Widespread PCV7 Vaccination, JID, 2007, vol. 196, pp. 1346-1354.

Kyaw et al., Effect of Introduction of the Pneumococcal Conjugate Vaccine on Drug-Resistant *Streptococcus pneumoniae*, N Engl J Med, 2006, vol. 354, No. 14, pp. 1455-1463.

O'Brien et al., "Potential Impact of Conjugate Pneumococcal Vaccines on Pediatric Pneumococcal Diseases", Am J. Epidemiol, 2004, vol. 159, No. 7, pp. 634-644.

Prymula et al., "Pneumococcal Capsular Polysaccharides Conjugated to Protein D for Prevention of Acute Otitis Media Caused By Both *Streptococcus pneumoniae* and Non—Typable Haemophilus Influenzae: A Randomised Double-blind Efficacy Study", 2006, vol. 367, pp. 740-748.

Skinner et al., "Pre-clinical Evaluation of a 15-Valent Pneumococcal Conjugate Vaccine (PCV15-CRM197) In an Infant-Rhesus Monkey Immunogenicity Model", 2011, vol. 29, pp. 8870-8876.

Traore et al., "Incidence, Seasonality, Age Distribution, and Mortality of Pneumococcal Meningitis in Burkina Faso and Togo", Clinical Infectious Disease, 2009, vol. 48, pp. S181-S189.

Whitney et al., Decline in Invasive Pneumococcal Disease After the Introduction of Protein-Poloysacchairde Conjugate Vaccine, New England Journal of Medicine, 2003, vol. 348, No. 18, pp. 1737-1746.

Kieninger, D.M., "Safety & Immunologic Non-Inferiority of 13-Valent Pneumococcal Conjugate Vaccine Compared to 7-Valent Pneumococcal Conjugate Vaccine Given with Routine Vaccines in Healthy Infante", 48th Annual ICAAC/ISDA 46th Annual Meeting, Oct. 25-28, 2008 abstract only.

* cited by examiner

15-VALENT PNEUMOCOCCAL POLYSACCHARIDE-PROTEIN CONJUGATE VACCINE COMPOSITION

CROSS-REFERENCE TO RELATED APPLICATIONS

None

FIELD OF INVENTION

The present invention provides a multivalent immunogenic composition having 15 distinct polysaccharide-protein conjugates. Each conjugate consists of a capsular polysaccharide prepared from a different serotype of *Streptococcus pneumoniae* (1, 3, 4, 5, 6A, 6B, 7F, 9V, 14, 18C, 19A, 19F, 22F, 23F or 33F) conjugated to a carrier protein, preferably $CRM_{197}$. The immunogenic composition, preferably formulated as a vaccine on an aluminum -based adjuvant, provides broad coverage against pneumococcal disease, particularly in infants and young children.

BACKGROUND OF THE INVENTION

*Streptococcus pneumoniae* is a significant cause of serious disease world-wide. In 1997, the Centers for Disease Control and Prevention (CDC) estimated there were 3,000 cases of pneumococcal meningitis, 50,000 cases of pneumococcal bacteremia, 7,000,000 cases of pneumococcal otitis media and 500,000 cases of pneumococcal pneumonia annually in the United States. See Centers for Disease Control and Prevention, MMWR Morb Mortal Wkly Rep 1997, 46(RR-8):1-13. Furthermore, the complications of these diseases can be significant with some studies reporting up to 8% mortality and 25% neurologic sequelae with pneumococcal meningitis. See Arditi et al., 1998, Pediatrics 102:1087-97.

The multivalent pneumococcal polysaccharide vaccines that have been licensed for many years have proved valuable in preventing pneumococcal disease in adults, particularly, the elderly and those at high-risk. However, infants and young children respond poorly to unconjugated pneumococcal polysaccharides. The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000. Following universal use of Prevnar® in the United States, there has been a significant reduction in invasive pneumococcal disease in children due to the serotypes present in Prevnar®. See Centers for Disease Control and Prevention, MMWR Morb Mortal Wkly Rep 2005, 54(36):893-7. However, there are limitations in serotype coverage with Prevnar® in certain regions of the world and some evidence of certain emerging serotypes in the United States (for example, 19A and others). See O'Brien et al., 2004, Am J Epidemiol 159:634-44; Whitney et al., 2003, N Engl J Med 348:1737-46; Kyaw et al., 2006, N Engl J Med 354:1455-63; Hicks et al., 2007, J Infect Dis 196:1346-54; Traore et al., 2009, Clin Infect Dis 48:S181-S189.

U.S. Patent Application Publication No. US 2006/0228380 A1 describes a 13-valent pneumococcal polysaccharide-protein conjugate vaccine including serotypes 1, 3, 4, 5, 6A, 6B, 7F, 9V, 14, 18C, 19A, 19F and 23F. Chinese Patent Application Publication No. CN 101590224 A describes a 14-valent pneumococcal polysaccharide-protein conjugate vaccine including serotypes 1, 2, 4, 5, 6A, 6B, 7F, 9N, 9V, 14, 18C, 19A, 19F and 23F.

Other PCVs have covered 7, 10, 11, or 13 of the serotypes contained in PCV-15, but immune interference has been observed for some serotypes (e.g. lower protection for serotype 3 in GSK's PCV-11) and lower response rates to serotype 6B in Pfizer's PCV-13. See Prymula et al., 2006, Lancet 367:740-48 and Kieninger et al., Safety and Immunologic Non-inferiority of 13-valent Pneumococcal Conjugate Vaccine Compared to 7-valent Pneumococcal Conjugate Vaccine Given as a 4-Dose Series in Healthy Infants and Toddlers, presented at the 48th Annual ICAAC/ISDA 46th Annual Meeting, Washington D.C., Oct. 25-28, 2008.

SUMMARY OF THE INVENTION

The present invention provides an immunogenic composition comprising (1) a multivalent polysaccharide-protein conjugate mixture consisting of capsular polysaccharides from 15 different serotypes of *S. pneumoniae* conjugated to a carrier protein, and (2) a pharmaceutically acceptable carrier. More specifically, the present invention provides a 15-valent pneumococcal conjugate vaccine (PCV-15) composition comprising a multivalent polysaccharide-protein conjugate mixture consisting of capsular polysasccharides from serotypes 1, 3, 4, 5, 6A, 6B, 7F, 9V, 14, 18C, 19A, 19F, 22F, 23F, and 33F of *S. pneumoniae* conjugated to a carrier protein; and a pharmaceutically acceptable carrier. In one specific embodiment, the immunogenic composition contains capsular polysaccharides from serotypes 1, 3, 4, 5, 6A, 6B, 7F, 9V, 14, 18C, 19A, 19F, 22F, 23F and 33F and the carrier protein is $CRM_{197}$.

In certain embodiments, the composition further comprises an adjuvant. In certain embodiments, the adjuvant is an aluminum-based adjuvant, such as aluminum phosphate, aluminum sulfate or aluminum hydroxide. In a particular embodiment of the invention, the adjuvant is aluminum phosphate.

The present invention also provides a method of inducing an immune response to a *S. pneumoniae* capsular polysaccharide, comprising administering to a human an immunologically effective amount of the above immunogenic composition.

The present invention further provides an immunogenic composition administered as a single 0.5 mL dose formulated to contain: 2 μg of each polysaccharide, except for 6B at 4 μg; about 32 μg $CRM_{197}$ carrier protein; 0.125 mg of elemental aluminum (0.5 mg aluminum phosphate) adjuvant; 150 mM sodium chloride and 20 mM L-histidine buffer.

DETAILED DESCRIPTION OF THE INVENTION

Figure 1:
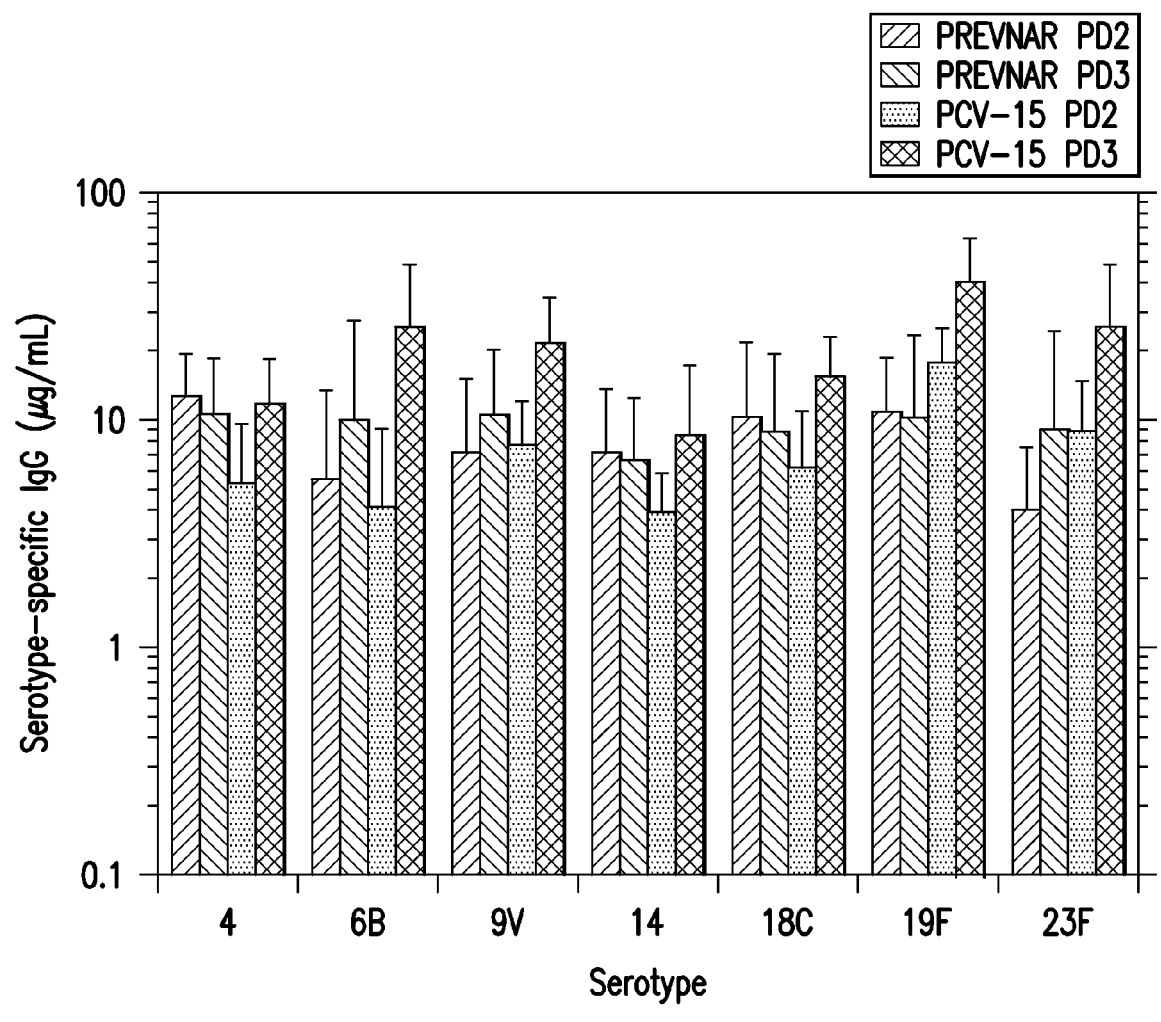
FIG. 1: Comparison of GMCs for PCV-15 relative to Prevnar® in Infant Rhesus Monkeys (Prevnar serotypes, PD-2 and PD-3). Error bars denote 2 standard errors.

The present invention provides a multivalent immunogenic composition comprising, consisting essentially of, or alternatively, consisting of 15 distinct polysaccharide-protein conjugates, wherein each of the conjugates contains a different capsular polysaccharide conjugated to a carrier protein, and wherein the capsular polysaccharides are prepared from serotypes 1, 3, 4, 5, 6A, 6B, 7F, 9V, 14, 18C, 19A, 19F, 22F, 23F and 33F of *S. pneumoniae*, together with a pharmaceutically acceptable carrier. In certain embodiments, the carrier protein is $CRM_{197}$. The immunogenic composition may further comprise an adjuvant, such as an aluminum-based adjuvant, such as aluminum phosphate, aluminum sulfate and aluminum hydroxide. The present invention also provides a method of inducing an immune response to a *S. pneumoniae* capsular polysaccharide conjugate, comprising administering to a human an immunologically effective amount of the above multivalent immunogenic composition.

As illustrated in the Examples, infra., preclinical studies in infant rhesus monkeys demonstrated robust antibody responses to all 15 serotypes in PCV-15 which are comparable to the responses for the 7 common serotypes in Prevnar®. Applicants' finding that a 15 valent pneumococcal conjugate vaccine including the addition of new polysaccharide-protein conjugates containing serotypes 22F and 33F provides robust antibody responses demonstrates the feasibility of expanding coverage of pneumococcal serotypes not covered by existing pneumococcal vaccines.

The term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those 15 particular *S. pneumoniae* polysaccharide protein conjugates and no other *S. pneumoniae* polysaccharide protein conjugates from a different serotype.

*Streptococcus pneumoniae* Capsular Polysaccharide—Protein Conjugates

Capsular polysaccharides from *Streptococcus pneumoniae* can be prepared by standard techniques known to those skilled in the art. For example, polysaccharides can be isolated from bacteria and may be sized to some degree by known methods (see, e.g., European Patent Nos. EP497524 and EP497525) and preferably by microfluidisation. Polysaccharides can be sized in order to reduce viscosity in polysaccharide samples and/or to improve filterability for conjugated products. In the present invention, capsular polysaccharides are prepared from serotypes 1, 3, 4, 5, 6A, 6B, 7F, 9V, 14, 18C, 19A, 19F, 22F, 23F and 33F of *S. pneumoniae*.

In one embodiment, each pneumococcal polysaccharide serotype is grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112.

Carrier proteins are preferably proteins that are non-toxic and non-reactogenic and obtainable in sufficient amount and purity. A carrier protein can be conjugated or joined with a *S. pneumoniae* polysaccharide to enhance immunogenicity of the polysaccharide. Carrier proteins should be amenable to standard conjugation procedures. In a particular embodiment of the present invention, $CRM_{197}$ is used as the carrier protein. In one embodiment, each capsular polysaccharide is conjugated to the same carrier protein (each capsular polysaccharide molecule being conjugated to a single carrier protein). In another embodiment, the capsular polysaccharides are conjugated to two or more carrier proteins (each capsular polysaccharide molecule being conjugated to a single carrier protein). In such an embodiment, each capsular polysaccharide of the same serotype is typically conjugated to the same carrier protein.

$CRM_{197}$ is a non-toxic variant (i.e., toxoid) of diphtheria toxin. In one embodiment, it is isolated from cultures of *Corynebacterium diphtheria* strain C7 (β197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultrafiltration, ammonium sulfate precipitation, and ion-exchange chromatography. In some embodiments, $CRM_{197}$ is prepared in *Pseudomonas fluorescens* using Pfenex Expression Technology™ (Pfenex Inc., San Diego, Calif.).

Other suitable carrier proteins include additional inactivated bacterial toxins such as DT (Diphtheria toxoid), TT (tetanus toxid) or fragment C of TT, pertussis toxoid, cholera toxoid (e.g., as described in International Patent Application Publication No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal adhesin protein (PsaA), C5a peptidase from Group A or Group B streptococcus, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can be used, such as CRM176, CRM228, CRM 45 (Uchida et al., 1973, J Biol Chem 218: 3838-3844); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711.

The purified polysaccharides are chemically activated to make the saccharides capable of reacting with the carrier protein. Once activated, each capsular polysaccharide is separately conjugated to a carrier protein to form a glycoconjugate. The polysaccharide conjugates may be prepared by known coupling techniques.

In one embodiment, the chemical activation of the polysaccharides and subsequent conjugation to the carrier protein are achieved by means described in U.S. Pat. Nos. 4,365,170, 4,673,574 and 4,902,506. Briefly, that chemistry entails the activation of pneumococcal polysaccharide by reaction with any oxidizing agent which oxidizes a terminal hydroxyl group to an aldehyde, such as periodate (including sodium periodate, potassium periodate, or periodic acid). The reaction leads to a random oxidative cleavage of vicinal hydroxyl groups of the carbohydrates with the formation of reactive aldehyde groups.

Coupling to the protein carrier (e.g., $CRM_{197}$) can be by reductive amination via direct amination to the lysyl groups of the protein. For example, conjugation is carried out by reacting a mixture of the activated polysaccharide and carrier protein with a reducing agent such as sodium cyanoborohydride. Unreacted aldehydes are then capped with the addition of a strong reducing agent, such as sodium borohydride.

In another embodiment, the conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in International Patent Application Publication Nos. WO 93/15760, WO 95/08348 and WO 96/29094; and Chu et al., 1983, Infect. Immunity 40:245-256.

Other suitable techniques use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction of with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In one embodiment, prior to formulation, each pneumococcal capsular polysaccharide antigen is individually purified from *S. pneumoniae*, activated to form reactive aldehydes, and then covalently conjugated using reductive amination to the carrier protein $CRM_{197}$.

After conjugation of the capsular polysaccharide to the carrier protein, the polysaccharide-protein conjugates are purified (enriched with respect to the amount of polysaccharide-protein conjugate) by one or more of a variety of techniques. Examples of these techniques are well known to the skilled artisan and include concentration/diafiltration operations, ultrafiltration, precipitation/elution, column chromatography, and depth filtration. See, e.g., U.S. Pat. No. 6,146,902.

Pharmaceutical/Vaccine Compositions

The present invention further provides compositions, including pharmaceutical, immunogenic and vaccine compositions, comprising, consisting essentially of, or alternatively, consisting of 15 distinct polysaccharide-protein conjugates, wherein each of the conjugates contains a different capsular polysaccharide conjugated to a carrier protein, and wherein the capsular polysaccharides are prepared from serotypes 1, 3, 4, 5, 6A, 6B, 7F, 9V, 14, 18C, 19A, 19F, 22F, 23F and 33F of *S. pneumoniae*, together with a pharmaceutically acceptable carrier and an adjuvant. These pneumococcal conjugates are prepared by separate processes and bulk formulated into a single dosage formulation.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094, trehalose dimycolate (TDM), and cell wall skeleton (CWS), preferably MPL+ CWS (Detox™); and (d) a Montanide ISA;

(3) saponin adjuvants, such as Quil A or STIMULON™ QS-21 (Antigenics, Framingham, Mass.) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion (5) synthetic polynucleotides such as oligonucleotides containing CpG motif(s) (U.S. Pat. No. 6,207,646); and (6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, alhydrogel, Superfos, Amphogel, aluminum (III) hydroxide, aluminum hydroxyphosphate sulfate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a target aggregate particle size in the range of 2-8 μm. The product is then diafiltered against physiological saline and steam sterilized.

In certain embodiments, a commercially available Al(OH)$_3$ (e.g. Alhydrogel or Superfos of Denmark/Accurate Chemical and Scientific Co., Westbury, N.Y.) is used to adsorb proteins in a ratio of 50-200 g protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of Ag that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted to target 8 μg/mL for all serotypes except 6B, which will be diluted to target 16 μg/mL. Once diluted, the batch will be filter sterilized, and an equal volume of aluminum phosphate adjuvant added aseptically to target a final aluminum concentration of 250 μg/mL. The adjuvanted, formulated batch will be filled into single-use, 0.5 mL/dose vials.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations of the present invention can be used to protect or treat a human susceptible to pneumococcal infection, by means of administering the vaccine via a systemic or mucosal route. In one embodiment, the present invention provides a method of inducing an immune response to a S. pneumoniae capsular polysaccharide conjugate, comprising administering to a human an immunologically effective amount of an immunogenic composition of the present invention. In another embodiment, the present invention provides a method of vaccinating a human against a pneumococcal infection, comprising the step of administering to the human an immunogically effective amount of a immunogenic composition of the present invention.

"Effective amount" of a composition of the invention refers to a dose required to elicit antibodies that significantly reduce the likelihood or severity of infectivitiy of S. pneumoniae during a subsequent challenge.

The methods of the invention can be used for the prevention and/or reduction of primary clinical syndromes caused by S. pneumoniae including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, each dose will comprise 0.1 to 100 μg of each polysaccharide, particularly 0.1 to 10 μg, and more particularly 1 to 5 μg. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 μg.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 μg, or 1, 1.2, 1.5, 2, 3, 5 mg or more. In yet another embodiment, the dose of alum salt described above is per μg of recombinant protein.

In a particular embodiment of the present invention, the PCV-15 vaccine is a sterile liquid formulation of pneumococcal capsular polysaccharides of serotypes 1, 3, 4, 5, 6A, 6B, 7F, 9V, 14, 18C, 19A, 19F, 22F, 23F and 33F individually conjugated to $CRM_{197}$. Each 0.5 mL dose is formulated to contain: 2 μg of each saccharide, except for 6B at 4 μg; about 32 μg $CRM_{197}$ carrier protein (e.g., 32 μg±5 μg, ±3 μg, ±2 μg, or ±1 μg); 0.125 mg of elemental aluminum (0.5 mg aluminum phosphate) adjuvant; and sodium chloride and L-histidine buffer. The sodium chloride concentration is about 150 mM (e.g., 150 mM±25 mM, ±20 mM, ±15 mM, ±10 mM, or ±5 mM) and about 20 mM (e.g, 20 mM±5 mM, ±2.5 mM, ±2 mM, ±1 mM, or ±0.5 mM) L-histidine buffer.

According to any of the methods of the present invention and in one embodiment, the subject is human. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

In one embodiment of the methods of the present invention, a composition of the present invention is administered as a single inoculation. In another embodiment, the vaccine is administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by S. pneumoniae is 2, 4, 6 and 12-15 months of age. Thus, in a preferred embodiment, the composition is administered as a 4-dose series at 2, 4, 6, and 12-15 months of age.

The compositions of this invention may also include one or more proteins from S. pneumoniae. Examples of S. pneumoniae proteins suitable for inclusion include those identified in International Patent Application Publication Nos. WO 02/083855 and WO 02/053761.

Formulations

The compositions of the invention can be administered to a subject by one or more method known to a person skilled in the art, such as parenterally, transmucosally, transdermally, intramuscularly, intravenously, intra-dermally, intra-nasally, subcutaneously, intra-peritonealy, and formulated accordingly.

In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of TRIS, acetate, glutamate, lactate, maleate, tartrate, phosphate, citrate, carbonate, glycinate, histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, and Polysorbate-80 are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations of the invention may also contain a surfactant. Preferred surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. A preferred surfactant for including in the emulsion is Tween 80 (polyoxyethylene sorbitan monooleate).

Mixtures of surfactants can be used, e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. Such modifications may increase the compound's solubility in aqueous solution, eliminate aggregation, enhance the physical and chemical stability of the compound, and greatly reduce the reactogenicity of the compound. In another embodiment, the desired in vivo biological activity is achieved by the administration of such polymer-compound abducts less frequently or in lower doses than with the unmodified compound.

In a preferred embodiment, the vaccine composition is formulated in L-histidine buffer with sodium chloride.

Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLES

Example 1

Preparation of *S. Pneumoniae* Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EPO497524. Isolates of pneumococcal subtypes are available from the ATCC.

The bacteria are identified as encapsulated, non-motile, Gram-positive, lancet-shaped diplococci that are alpha-hemolytic on blood-agar. Subtypes are differentiated on the basis of Quelling reaction using specific antisera. See, e.g., U.S. Pat. No. 5,847,112.

Cell Banks

Cell banks representing each of the *S. pneumococcus* serotypes present in PCV-15 were obtained from the Merck Culture Collection (Rahway, N.J.) in a frozen vial.

Inoculation

A thawed seed culture was transferred to the seed fermentor containing an appropriate pre-sterilized growth media.

Seed Fermentation

The culture was grown in the seed fermentor with temperature and pH control. The entire volume of the seed fermentor was transferred to the production fermentor containing pre-sterilized growth media.

Production Fermentation

The production fermentation was the final cell growth stage of the process. Temperature, pH and the agitation rate was controlled.

Inactivation

The fermentation process was terminated via the addition of an inactivating agent. After inactivation, the batch was transferred to the inactivation tank where it was held at controlled temperature and agitation.

Purification

Cell debris was removed using a combination of centrifugation and filtration. The batch was ultrafiltered and diafiltered. The batch was then subjected to solvent-based fractionations that remove impurities and recover polysaccharide.

Example 2

Preparation of Pneumococcal Polysaccharide-$CRM_{197}$ Conjugates

Activation Process

The different serotype saccharides are individually conjugated to the purified $CRM_{197}$ carrier protein using a common process flow. In this process the saccharide is dissolved, sized to a target molecular mass, chemically activated and buffer-exchanged by ultrafiltration. The purified $CRM_{197}$ is then conjugated with the activated saccharide and the resulting conjugate is purified by ultrafiltration prior to a final 0.2 µm membrane filtration. Several process parameters within each step, such as pH, temperature, concentration, and time are serotype-specific as described in this example.

Step 1: Dissolution

Purified polysaccharide was dissolved in water to a concentration of 2-3 mg/mL. The dissolved polysaccharide was passed through a mechanical homogenizer with pressure preset from 0-1000 bar. Following size reduction, the saccharide was concentrated and diafiltered with sterile water on a 10 kDa MWCO ultrafilter. The permeate was discarded and the retentate was adjusted to a pH of 4.1 with a sodium acetate buffer, 50 mM final concentration. For serotypes 4 and 5, 100 mM sodium acetate at pH 5.0 was used. For serotype 4, the solution was incubated at 50°±2° C. Hydrolysis was stopped by cooling to 20-24° C.

Step 2: Periodate Reaction

The required sodium periodate molar equivalents for pneumococcal saccharide activation was determined using total saccharide content. With thorough mixing, the oxidation was allowed to proceed between 3-20 hours at 20-24° C. for all serotypes except 5, 7F, and 19F for which the temperature was 2-6° C.

Step 3: Ultrafiltration

The oxidized saccharide was concentrated and diafiltered with 10 mM potassium phosphate, pH 6.4 (10 mM sodium acetate, pH 4.3 for serotype 5) on a 10 kDa MWCO ultrafilter. The permeate was discarded and the retentate was adjusted to a pH of 6.3-8.4 by addition of 3 M potassium phosphate buffer.

Conjugation Process

Step 1: Conjugation Reaction

The concentrated saccharide was mixed with $CRM_{197}$ carrier protein in a 0.2-2 to 1 charge ratio. The blended saccharide-$CRM_{197}$ mixture was filtered through a 0.2 µm filter.

The conjugation reaction was initiated by adding a sodium cyanoborohydride solution to achieve 1.8-2.0 moles of sodium cyanoborohydride per mole of saccharide. The reaction mixture was incubated for 48-120 hours at 20-24° C. (8-12° C. for serotypes 3, 5, 6A, 7F, 19A, and 19F).

Step 2: Borohydride Reaction

At the end of the conjugation incubation the reaction mixture was adjusted to 4-8° C., and a pH of 8-10 with either 1.2 M sodium bicarbonate buffer or 3 M potassium phosphate buffer (except serotype 5). The conjugation reaction was stopped by adding the sodium borohydride solution to achieve 0.6-1.0 moles of sodium borohydride per mole of saccharide (0 moles of borohydride added for serotype 5). The reaction mixture was incubated for 45-60 minutes.

Step 3: Ultrafiltration Steps

The reaction mixture was diafiltered on a 100 kDa MWCO ultrafilter with a minimum of 20 volumes of 100 mM potassium phosphate, pH 8.4 buffer. The retentate from the 100 kDa ultrafilter was diafiltered on a 300 kDa MWCO ultrafilter with a minimum of 20 diavolumes of 150 mM sodium chloride at 20-24° C. The permeate was discarded.

Step 4: Sterile Filtration

The retentate from the 300 kDa MWCO diafiltration was filtered through a 0.2 µm filter and filled into borosilicate glass containers at appropriate volumes for release testing, in-process controls, and formulation (except serotype 19F). The serotype 19F conjugate was passed through a 0.2 µm filter into a holding tank and incubated at 20-24° C. Following incubation, the conjugate was diafiltered on a 300 kDa MWCO ultrafilter with a minimum of 20 diavolumes of 150 mM sodium chloride at 20-24° C. The permeate was discarded, and the retentate was filtered through a 0.2 µm filter and filled into borosilicate glass containers at appropriate volumes for release testing, in-process controls, and formulation. The final bulk concentrates were stored at 2-8° C.

Example 3

Formulation of a 15-valent Pneumococcal Conjugate Vaccine

The required volumes of bulk concentrates were calculated based on the batch volume and the bulk saccharide concentrations. The combined 15 conjugates were further diluted to a target adsorption concentration by the addition of a sodium chloride and L-histidine, pH 5.8, containing buffer. After sufficient mixing, the blend was sterile filtered through a 0.2 µm membrane. The sterile formulated bulk was mixed gently during and following its blending with bulk aluminum phosphate. The formulated vaccine was stored at 2-8° C.

In an alternate process, the combined 15 conjugates were further diluted to a target concentration by the addition of a sodium chloride and L-histidine, pH 5.8, containing buffer. Polysorbate 80 was added to a final concentration of 0.005%, to the diluted buffered conjugate mixture prior to sterile filtration. Following sterile filtration, the formulated vaccine was stored at 2-8° C.

Table 1 shows the final composition of the adjuvanted and non-adjuvanted form of PCV-15.

TABLE 1

Composition of Adjuvanted and Non-Adjuvanted 15 - valent Pneumococcal Conjugate Vaccine Formulations

| | | Clinical Formulations, unit/0.5 mL dose | |
|---|---|---|---|
| Description of Ingredients | | Adjuvanted PCV-15 | Non-adjuvanted PCV-15 |
| Active Ingredients | Pneumococcal polysaccharide antigens | 32 µg of total polysaccharide (2 µg of each of the following polysaccharide serotypes 1, 3, 4, 5, 6A, 7F, 9V, 14, 18C, 19A, 19F, 22F, 23F, 33F; 4 µg of serotype 6B polysaccharide) | 32 µg of total polysaccharide (2 µg of each of the following polysaccharide serotypes 1, 3, 4, 5, 6A, 7F, 9V, 14, 18C, 19A, 19F, 22F, 23F, 33F; 4 µg of serotype 6B polysaccharide)) |
| Other Ingredients | Carrier protein $CRM_{197}$ | ~32 µg | ~32 µg |
| | Aluminum (µg)[a] | 125 | 0 |
| | Polysorbate-80 (µg) | 0 | 2.5 |
| | L-histidine (mM) | 20 | 20 |
| | Sodium Chloride (mM) | 150 | 150 |
| | Water for Injection | Q.S.[b] | Q.S.[b] |

[a]Quantity of elemental aluminum in APA.
[b]Quantify sufficient to 0.5 mL.

Example 4

Immunogenicity Studies

Experiments were designed to evaluate the immunogenicity of multiple formulations of pneumococcal conjugate vaccines in the infant rhesus monkeys (IRM) and New Zealand White Rabbits (NZWR) animal models. Experiments in infant rhesus monkeys were designed to closely match the recommended schedule for pneumococcal conjugate vaccine in United States, with the infant series given at 2, 4, and 6 months of age. Thus, infant rhesus monkeys were immunized starting at 2-3 months of age and administered vaccine at 2-month intervals. The 4th dose, which is also part of the recommended schedule for U.S. children was not administered. Adult rabbits (NZWR) were used to evaluate multiple vaccine formulations. NZWR studies were performed using two vaccine doses given in an accelerated (2-week interval) immunization regimen. For the preclinical evaluation of immune responses, a full human dose was delivered to rabbits whereas infant monkeys received a half-human dose. The rationale for selecting a half-human dose for infant monkeys was due to limitations in the volume that can be administered to infant rhesus monkeys in a single intramuscular site.

Assessment of Serotype-specific IgG Responses

A multiplexed electrochemiluminescence (ECL) assay was developed for use with rabbit and rhesus monkey serum based on a human assay using Meso Scale Discovery (MSD) technology which utilizes a SULFO-TAG™ label that emits light upon electrochemical stimulation. See Marchese et al., 2009, Clin Vaccine Immunol 16:387-96. Using a dedicated ECL plate reader, an electrical current is placed across the plate-associated electrodes resulting in a series of electrically induced reactions leading to luminescent signal. The multispot configuration used in development and validation was 10 spots/well in a 96-well plate—format, and each well was coated with 5 ng pneumococcal (Pn) polysaccharide (Ps) per spot. Two plate formats were used to ensure that crossreacting polysaccharides (i.e., 6A and 6B, and 19A and 19F) were tested in separate plates. Plate format 1 contained serotypes 3, 4, 6B, 9V, 14, 18C, 19F, and 23F whereas plate format 2 contained serotypes 1, 5, 6A, 7F, 19A, 22F and 33F. Each well also contained two bovine serum albumin (BSA) spots which were used to assess the background reactivity of the assay (i.e., the response associated with serum and labeled secondary antibody in the absence of PnPs). Assay standard (89SF-2), controls, and test sera were diluted to appropriate levels in phosphate buffered saline (PBS) containing 0.05% Tween 20, 1% BSA, 5 µg/ml C-polysaccharide (CPs), 10 µg/ml serotype 25 polysaccharide (PnPs25) and 10 µg/ml serotype 72 polysaccharide (PnPs72) and incubated overnight at 4° C. (2 to 8° C.) or at ambient temperature for 45 minutes. Human antibody reagents and standards were used when testing the infant monkey samples whereas SULFO-TAG™-labeled anti-rabbit IgG was used as the secondary antibody when testing rabbit serum samples. Each antigen coated plate was incubated at ambient temperature for 1 hour on a shaker platform with blocking agent. Plates were washed with 0.05% PBS-T and 25 µL per well of the pre-adsorbed and diluted test sera was added and incubated for 45 min at ambient temperature on a shaker platform. Plates were washed with 0.05% PBS-T and then MSD SULFO-TAG™ labeled-goat anti-human IgG secondary antibody (for rhesus monkey serum) and labeled goat anti-rabbit IgG secondary antibody (for rabbit serum) was added to each well and incubated 1 hour at ambient temperature on a shaker platform. Plates were washed with 0.05% PBS-T and 150 µL of MSD Read Buffer-T 4x (with surfactant) diluted 1:4 in water added to each well. The plates were read using a MSD Sector Imager Model No. 2400 or 6000. For rabbit studies, the results are presented as geometric mean titers (GMTs) or ratios of GMTs. For infant rhesus monkey studies, the results were expressed as geometric mean concentrations read from a standard curve using the serotype-specific IgG concentrations assigned to the human reference standard (89 SF-2).

Assessment of Functional (Opsonophagocytic) Responses

Samples from infant rhesus monkey study 2 were tested in a 4-plexed MOPA assay (MOPA-4). See Burton et al., 2006, Clin Vaccine Immunol 13:1004-9. The assay uses bacterial strains selected to be resistant to one of 4 antibiotics so that the first part of the assay (opsonization and uptake into differentiated HL-60 cells) can be performed with up to 4 serotypes at a time. The read-out for bacterial killing is done in parallel in the presence of each of the 4 antibiotics to which the corresponding strains are resistant in order to determine killing titers for each specific serotype. Results are expressed as the reciprocal dilution at which 50% killing is observed (after interpolation).

Statistical Methodology for Preclinical Studies

Both animal models have limitations related to sample size. In general, 8 infant monkeys or 8 rabbits were used per study arm. With 8 animals per arm a critical fold difference in geometric mean titer between treatment arms of 2.5 fold was regarded as a meaningful response threshold. The 2.5-fold difference was determined based on the assumption that for each serotype, the standard deviation of the natural log transformed titers within a treatment arm is ln(2). Letting $\overline{Y}_i$ denote the mean of the ln transformed titers in the $i^{th}$ treatment arm, $n_i$ the number of animals within the $i^{th}$ treatment arm, $\sigma_i^2$ the known variance of the ln transformed titers among animals within the $i^{th}$ treatment arm, and setting $n_i=8$ and $\sigma_i^2=(\ln(2))^2$ for all i, then the value of 2.5 is obtained by solving for $e^{\overline{Y}_j-\overline{Y}_k}$ where $$\frac{\overline{Y}_j - \overline{Y}_k}{\sqrt{\frac{\sigma_j^2}{n_j} + \frac{\sigma_k^2}{n_k}}} = Z_{0.995},$$

and $Z_{0.995}$ denotes the inverse of the standard normal cumulative distribution, with a probability of 0.995 (i.e., $Z_{0.995}=2.576$). Note that the calculated value of 2.44 is rounded to 2.5 as 2.5 also provides for a convenient reciprocal in 0.4.

Serotype-specific IgG Response of Infant Rhesus Monkeys (IRMs) to PCV-15

A pilot immunogenicity study (IRM-1) was conducted to determine whether infant rhesus monkeys (IRMs) would be a good model in which to evaluate Pn polysaccharide $CRM_{197}$ conjugate vaccines. The primary goal of the experiment was to determine whether IRMs (like human infants) would be unresponsive to free Pn polysaccharides but respond well to conjugate vaccines. Groups of 5 IRMs were injected starting at 2-3 months of age with either Pn polysaccharide, Prevnar® or PCV-15. Three doses of vaccine were administered intramuscularly (IM) at 2 month intervals, and serotype-specific IgG responses were measured prior to the first dose and at 1 month postdose 2 and at 1 month postdose 3 using a multiarray electrochemiluminescence (ECL) assay (data not shown). The results indicated that IRMs responded poorly, if at all, to free Pn polysaccharide but very well to the conjugate vaccines. The results indicated that induction of an IgG response to Pn polysaccharides in infant rhesus monkeys was dependent upon conjugation of the polysaccharides to a carrier protein and therefore was a classic T-cell dependent response. Thus, the IRM model was determined to be suitable for evaluating PCV-15 formulations.

which is not in the vaccine. Prevnar® induced high OPA titers and a 100% response rate for all serotypes contained in that vaccine, but it induced only a weak crossreactive response to serotypes 6A and 6C in a fraction of monkeys.

TABLE 2

Serotype-Specific OPA GMTs in Infant Rhesus Monkeys after Vaccination with PCV-15 or Prevnar ®
(Pre-vaccination, PD-2, and PD-3 geometric mean titers and PD-3 percent responders with a titer ≧8)

|  | Prevnar | | | | PCV-15 | | | |
| --- | --- | --- | --- | --- | --- | --- | --- | --- |
| Serotype | Pre | PD-2 | PD-3 | PD-3 Responders (titers ≧8) | Pre | PD-2 | PD-3 | PD-3 Responders (titers ≧8) |
| 1 | n.d. | n.d. | n.d. | n.d. | 4 | 65 | 340 | 100% |
| 3 | n.d. | n.d. | n.d. | n.d. | 5 | 1442 | 1548 | 100% |
| 4 | 4 | 11459 | 5004 | 100% | 4 | 5280 | 3453 | 100% |
| 5 | 4 | 4 | 4 | 0% | 4 | 1879 | 1719 | 100% |
| 6A | 4 | 21 | 113 | 57% | 4 | 1188 | 7807 | 100% |
| 6B | 8 | 8294 | 6043 | 100% | 4 | 2477 | 9601 | 100% |
| *6C* | *4* | *11* | *16* | *29%* | *4* | *1038* | *5134* | *100%* |
| 7F | 4 | 4 | 71 | 43% | 4 | 7541 | 10092 | 100% |
| 9V | 4 | 1779 | 748 | 100% | 4 | 625 | 1297 | 100% |
| 14 | 8 | 12395 | 7782 | 100% | 4 | 11366 | 9891 | 100% |
| 18C | 4 | 5571 | 1718 | 100% | 4 | 1934 | 1701 | 100% |
| 19A | 4 | 15 | 4 | 0% | 4 | 2210 | 1895 | 100% |
| 19F | 4 | 1365 | 432 | 100% | 4 | 2555 | 4021 | 100% |
| 22F | n.d. | n.d. | n.d. | n.d. | 4 | 2489 | 7298 | 100% |
| 23F | 4 | 1789 | 2126 | 100% | 4 | 3093 | 2465 | 100% |
| 33F | n.d. | n.d. | n.d. | n.d. | 4 | 14 | 11548 | 100% |

Note:
Serotypes contained in Prevnar are bolded.
Results for serotype 6C are shown in italics since that serotype is not contained in PCV-15.
n.d. not determined A second study (IRM-2) was conducted to evaluate a formulation of PCV-15 using a bulk conjugation process that minimized free (unconjugated) polysaccharide and unconjugated $CRM_{197}$. FIG. 1 shows the postdose 2 (PD-2) and postdose 3 (PD-3) IgG responses to PCV-15 versus Prevnar® for the 7 serotypes contained in Prevnar® (4, 6B, 9V, 14, 18C, 19F, 23F). PD-2 responses to PCV-15 were equivalent or slightly lower than the corresponding responses to Prevnar® whereas PD-3 responses to PCV-15 were somewhat higher than those elicited by Prevnar® for nearly all serotypes.

Figure 2:
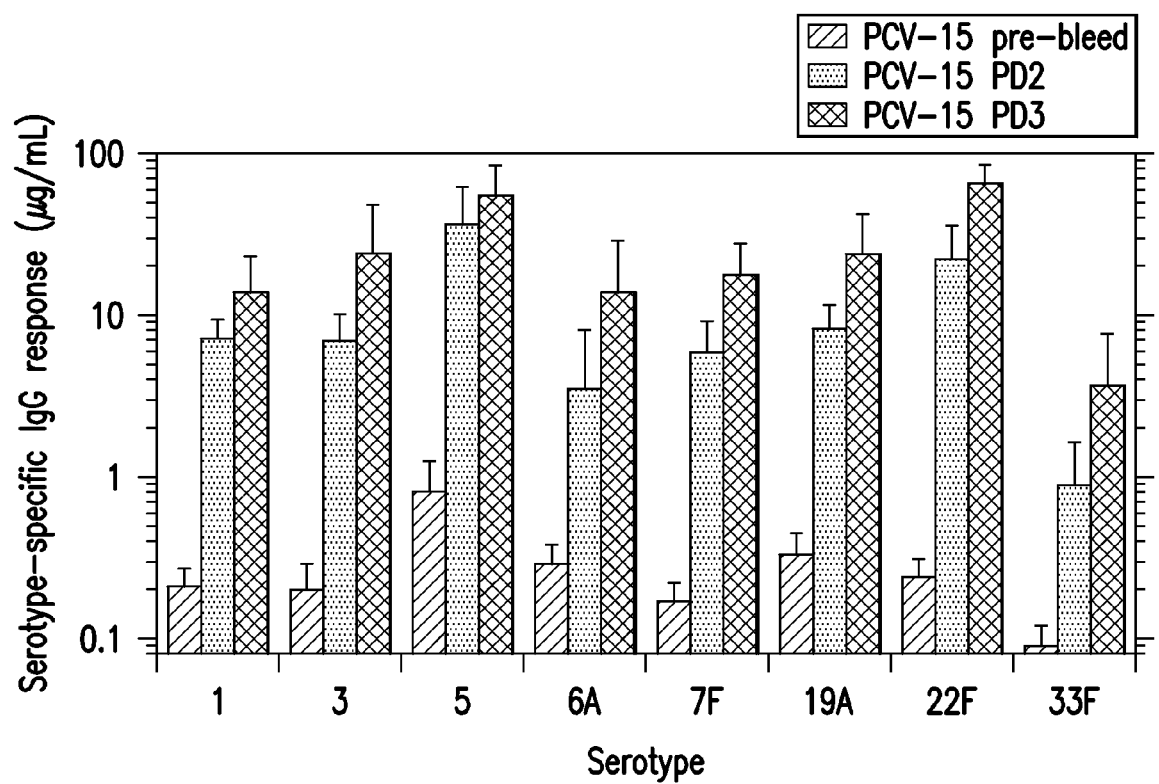
FIG. 2: Serotype-specific GMCs to non-Prevnar® serotypes in infant rhesus monkeys immunized with PCV-15. Error bars denote 2 standard errors.

IRM responses to the non-Prevnar serotypes in PCV-15 are shown in FIG. 2. PD-2 responses to the non-Prevnar serotypes in PCV-15 were all at least 10-fold higher than baseline (pre-vaccination) IgG concentrations, and titers continued to rise at PD-3.

The results indicate that antibody responses to PCV-15 and Prevnar® were comparable for the 7 common serotypes and that post-vaccination responses to PCV-15 were >10-fold higher than baseline for the 8 added serotypes.

Functional (Opsonophagocytic) Immune Response of IRMs to PCV-15

In order to determine whether PCV-15 induced functional antibody responses in infant monkeys, an opsonophagocytic killing (OPA) assay was performed on sera from IRM-2. Pre-vaccination, PD-2, and PD-3 responses to PCV-15 and Prevnar® are shown in Table 2. The results shown are the GMTs from serum samples from 7-8 monkeys per time point assayed in duplicate. Also shown are the percent responders (i.e., those with OPA titers ≧8) at the PD-3 time point. PCV-15 induced a high PD-2 GMT for all serotypes except types 1 and 33F. After 3 vaccine doses, PCV-15 induced high OPA GMTs to each serotype and a 100% OPA response rate for all 15 serotypes contained in the vaccine. Of note, PCV-15 also induced a good crossreactive OPA response to serotype 6C, Evaluation of PCV-15 Formulations in New Zealand White Rabbits PCV-15 formulations were evaluated in 4 studies in adult New Zealand White Rabbits (NZWRs) using a compressed immunization regimen in which rabbits received a full human dose of vaccine at day 0 and day 14, and serum was collected at day 0, 14 and 28 for analysis. All studies were benchmarked with Prevnar®, and as summarized in Table 3 (NZWR Experiments 1-4).

Results are shown in Table 3 for Post-dose 2 responses of New Zealand white rabbits expressed as a ratio of the geometric mean IgG responses to Merck PCV-15 over Prevnar® for serotypes in common between the vaccines.

TABLE 3

Post-dose 2 IgG Response Ratios (PCV-15:Prevnar ™)
of Lead PCV-15 Formulations Tested in NZWR

| Serotype | NZWR-1 | NZWR-2 | NZWR-3 | NZWR-4 |
| --- | --- | --- | --- | --- |
| 4 | 0.70 | 0.59 | 0.63 | 1.06 |
| 6B | 1.35 | 0.49 | 1.53 | 0.45 |
| 9V | 2.07 | 1.79 | 1.70 | 1.31 |
| 14 | 2.37 | 0.58 | 2.32 | 2.55 |
| 18C | 0.87 | 0.6 | 0.52 | 0.27 |
| 19F | 0.66 | 0.76 | 2.70 | 1.25 |
| 23F | 0.36 | 0.30 | 1.22 | 0.41 |

Serotype-specific IgG responses were generally within 2.5-fold of the corresponding responses to Prevnar®. An exception was serotype (23F), which was >2.5-fold lower than that to Prevnar® in 2 of 4 experiments. The fold-rise in antibody levels to the non-Prevnar® serotypes from Day 0 to Day 28 (Post-dose 2, PD-2) are summarized in Table 4.

TABLE 4

Fold-rise (Post-dose 2:Pre-dose 1) in IgG Responses to Non-Prevnar ™
Serotypes of PCV-15 Lead Formulations Tested in NZWR

| Serotype | NZWR-1 | NZWR-2 | NZWR-3 | NZWR-4 |
|---|---|---|---|---|
| 1 | 14.9 | 30.5 | 55.1 | 59.9 |
| 3 | 33.6 | 16.2 | 61.5 | 28.5 |
| 5 | 12.8 | 70.2 | 112.0 | 134.0 |
| 6A | 21.3 | 77.8 | 143.0 | 123.0 |
| 7F | 42.0 | 83.8 | 194.0 | 108.0 |
| 19A | 40.5 | 79.1 | 450.0 | 314.0 |
| 22F | 45.7 | 87.8 | 243.0 | 135.0 |
| 33F | 21.7 | 47.9 | 98.8 | 69.4 |

Effect of Polysaccharide Conjugate Vaccine Dose on Immunogenicity in NZWRs

The immunogenicity of an increased dose (double dose, 2×) of polysaccharide conjugates was also evaluated for all serotypes contained in PCV-15 compared with the planned human dose (1×) of the vaccine. For the 2× polysaccharide conjugate formulation, the APA concentration was increased to 1.5× in order to assure that most of the conjugate would be bound to the aluminum adjuvant. As shown in Table 5, there did not appear to be a significant benefit in increasing the amount of polysaccharide-conjugate in the vaccine. Differences across all serotypes were within 2-fold., and the geometric mean fold-ratio (1×PCV-15/2×PCV-15+1.5×APA) was 1.1.

Effect of Aluminum Adjuvant on Immunogenicity of PCV-15 in NZWRs

The impact of aluminum adjuvant (APA) on antibody responses was evaluated in one rabbit study. PCV-15 formulated with the planned human dose of APA (PCV-15 1×APA), with double the planned human dose of APA (PCV-15 2×APA), and without any aluminum adjuvant (PCV-15 0×APA), were tested. A Prevnar® group was also included in the study.

The PD-2 results indicated that doubling the concentration of APA had little impact on the serotype-specific IgG response to PCV-15. The fold-difference in titer (1×APA/2×APA) ranged from 0.6 (serotype 6B) to 2.3 (serotype 22F) and geometric mean fold-ratio across the 15 serotypes was 1.1. In the absence of aluminum adjuvant antibody titers appeared lower for many of the serotypes relative to PCV-15 with 1×APA. The fold-difference in titer (1×/0×) ranged from 0.5 (serotype 5) to 2.9 (serotype 23F) and the geometric mean fold-ratio across the 15 serotypes was 1.4. Overall, there does not appear to be a genuine advantage to doubling the level of aluminum adjuvant and there appears to be a disadvantage to eliminating the adjuvant (Table 6) in this animal model.

The PD-2 results indicated that there was a decrease in antibody titers for many of the serotypes in the arm that did not contain Aluminum Phosphate Adjuvant (APA) when

TABLE 5

Post-dose 2 Geometric Mean IgG titers (95% confidence intervals) with Prevnar ®,
1x Human dose of PCV-15* or 2x Human Dose of PCV-15† in NZWR

| Serotype | Treatment Arm | | | Fold-Difference Ratio of 2x PCV-15/1x PCV-15 |
|---|---|---|---|---|
| | Prevnar ™ (n = 8) | 1x PCV-15 (n = 8) | 2x PCV-15 (n = 8) | |
| 4 | 736,400 (483200, 1122400) | 436,000 (199700, 951700) | 472,100 (246800, 902900) | 1.1 |
| 6B | 363,600 (205000, 644800) | 176,500 (72800, 427800) | 196,900 (85900, 451400) | 1.1 |
| 9V | 298,200 (173800, 511700) | 534,700 (362800, 788100) | 580,600 (366300, 920200) | 1.1 |
| 14 | 345,200 (200200, 595000) | 198,900 (94500, 418700) | 273,600 (229500, 326100) | 1.4 |
| 18C | 954,500 (815700, 1116800) | 573,000 (396900, 827400) | 455,900 (245100, 848000) | 0.8 |
| 19F | 720,100 (475700, 1090200) | 548,000 (367700, 816800) | 544,300 (269000, 1101400) | 1.0 |
| 23F | 816,300 (565100, 1179100) | 246,200 (117200, 517100) | 188,500 (78100, 454800) | 0.8 |
| 1 | 5,300 (3100, 9200) | 91,500 (62600, 133600) | 72,200 (46700, 111600) | 0.8 |
| 3 | 12,000 (8600, 16800) | 32,300 (19600, 53000) | 23,600 (14100, 39400) | 0.7 |
| 5 | 5,700 (4100, 7900) | 245,600 (114200, 528200) | 224,600 (136700, 369100) | 0.9 |
| 6A | 525,900 (275000, 1005600) | 186,700 (71300, 488600) | 251,800 (102300, 620100) | 1.3 |
| 7F | 4,600 (4000, 5200) | 326,900 (238000, 449000) | 212,200 (134200, 335500) | 0.6 |
| 19A | 432,800 (237800, 787800) | 260,900 (145500, 468000) | 276,100 (153200, 497600) | 1.1 |
| 22F | 6,000 (4400, 8100) | 359,800 (239000, 541700) | 345,300 (221200, 539000) | 1.0 |
| 33F | 6,600 (4700, 9300) | 177,400 (118300, 266200) | 138,500 (68300, 280900) | 0.8 |

Figure 3:
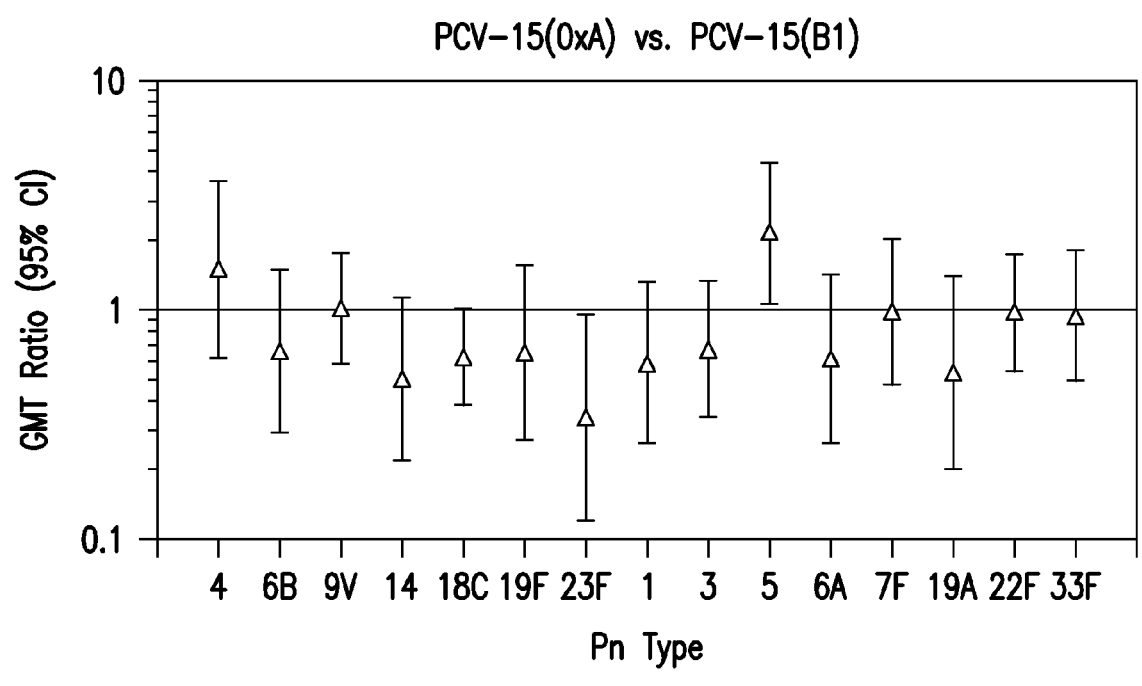
FIG. 3: NZWR-1: Comparison of geometric mean titers in rabbits immunized with PCV-15 without (0ΔA) or with APA (B1) (Post-dose 2). Error bars denote 95% CI on the geometric mean fold-difference (PCV-15 without APA/PCV-15 with APA).

*Formulated with 1x aluminum adjuvant (APA)
†Formulated with 1.5x APA compared to PCV-15 containing APA (FIG. 3) indicating a requirement for the inclusion of an aluminum adjuvant for optimal PCV-15 immunogenicity in rabbits. In addition, no benefit was found when double the amount of APA was included in the vaccine (data not shown).

TABLE 6

Post-dose 2 Geometric Mean IgG Titers (95% confidence intervals) of PCV-15 Formulated with 1x, 2x or 0x Aluminum Adjuvant (APA) in NZWR

| | Treatment Arm | | | | Fold Difference Relative to PCV-15 (1x APA) | |
|---|---|---|---|---|---|---|
| Sero | Prevnar ™ (n = 8) | PCV-15 1x APA (n = 8) | PCV-15 2x APA (n = 8) | PCV-15 0x APA (n = 6) | 1x/2x APA | 1x/0x APA |
| 4 | 380,700 (226100, 641000) | 268,400 (205100, 351200) | 196,200 (84000, 458800) | 404,600 (105500, 1550700) | 1.4 | 0.7 |
| 6B | 105,900 (59800, 187400) | 143,300 (90700, 226300) | 236,200 (102000, 547100) | 93,800 (46300, 189700) | 0.6 | 1.5 |
| 9V | 271,600 (177400, 415700) | 562,000 (382700, 825400) | 595,600 (390200, 908900) | 569,200 (239900, 1350500) | 0.9 | 1.0 |
| 14 | 142,500 (75200, 269700) | 337,600 (174000, 654900) | 453,000 (237400, 864400) | 167,600 (65100, 431700) | 0.7 | 2.0 |
| 18C | 323,000 (250400, 416500) | 282,200 (210400, 378500) | 248,700 (193900, 319000) | 175,200 (91800, 334000) | 1.1 | 1.6 |
| 19F | 302,500 (232700, 393200) | 199,800 (132200, 302100) | 243,400 (87600, 676600) | 127,700 (35100, 463700) | 0.8 | 1.6 |
| 23F | 328,200 (178200, 604300) | 117,200 (60300, 227700) | 77,600 (31300, 192300) | 40,200 (10100, 160900) | 1.5 | 2.9 |
| 1 | 5,600 (4400, 7200) | 91,700 (46800, 179800) | 67,800 (38900, 118100) | 53,300 (14800, 191600) | 1.4 | 1.7 |
| 3 | 6,300 (4800, 8100) | 156,100 (104800, 232500) | 155,700 (75300, 322200) | 104,000 (45000, 240000) | 1.0 | 1.5 |
| 5 | 4,800 (4000, 5700) | 81,700 (50800, 131300) | 60,700 (29100, 126400) | 176,100 (72100, 430300) | 1.3 | 0.5 |
| 6A | 84,500 (50300, 141900) | 163,600 (114000, 234900) | 226,800 (92500, 556200) | 99,300 (48800, 202000) | 0.7 | 1.6 |
| 7F | 5,200 (3300, 8400) | 216,800 (141500, 332000) | 282,100 (158200, 503200) | 212,200 (64200, 701900) | 0.8 | 1.0 |
| 19A | 95,100 (54300, 166700) | 238,300 (161000, 352700) | 207,400 (69800, 615900) | 125,700 (34000, 465100) | 1.1 | 1.9 |
| 22F | 6,500 (4900, 8500) | 348,900 (267200, 455500) | 149,400 (90100, 247600) | 336,800 (184200, 615700) | 2.3 | 1.0 |
| 33F | 7,100 (5000, 10100) | 235,600 (106500, 521300) | 163,600 (92700, 288800) | 222,000 (125100, 393800) | 1.4 | 1.1 |

Discussion and Conclusions

The preclinical data demonstrate that a formulation of PCV-15 (formulated on APA) is highly immunogenic in two species (infant rhesus monkeys and rabbits). Serotype-specific responses to PCV-15 were comparable to those elicited by Prevnar® for the 7 serotypes in common between the vaccines. For the 8 new serotypes in PCV-15, there was a robust response elicited in both infant rhesus monkeys and in rabbits, with ≧10-fold rise in IgG responses for all serotypes after 2 vaccine doses in both species. Limited dose-ranging experiments indicated that a 2-fold increase in the amount of polysaccharide conjugates did not result in an increased antibody response. Similarly, a 2-fold increase in aluminum adjuvant concentration did not appear to significantly improve the immunogenicity profile of PCV-15. Elimination of the adjuvant did, however, result in lower responses to some serotypes suggesting the potential need for an adjuvant in humans. Functional (OPA) antibody responses were elicited by PCV-15 to all 15 serotypes in the vaccine as well as to Serotype 6C, which is not a component of PCV-15.

What is claimed is:

1. An immunogenic composition comprising:
  (1) a multivalent polysaccharide-protein conjugate mixture having capsular polysaccharides from serotypes 1, 3, 4, 5, 6A, 6B, 7F, 9V, 14, 18C, 19A, 19F, 22F, 23F, and 33F of *Streptococcus pneumoniae* conjugated to $CRM_{197}$ and no other *S. pneumoniae* polysaccharide protein conjugates from a different serotype; and
  (2) a pharmaceutically acceptable carrier.

2. The immunogenic composition of claim 1, further comprising an adjuvant.

3. The immunogenic composition claim 2, wherein the adjuvant is an aluminum-based adjuvant.

4. The immunogenic composition of claim 3, wherein the adjuvant is selected from the group consisting of aluminum phosphate, aluminum sulfate and aluminum hydroxide.

5. The immunogenic composition of claim 4, wherein the adjuvant is aluminum phosphate.

6. A method of inducing an immune response to a *Streptococcus pneumoniae* capsular polysaccharide, comprising administering to a human an immunologically effective amount of the immunogenic composition of claim 1.

7. The method of claim 6, wherein the immunogenic composition administered is a single 0.5 mL dose formulated to contain: 2 μg of each saccharide, except for 6B at 4 μg; about 32 μg $CRM_{197}$ carrier protein; 0.125 mg of elemental aluminum (0.5 mg aluminum phosphate) adjuvant; 150 mM sodium chloride and 20 mM L-histidine buffer.

* * * * *